US009447020B2

(12) United States Patent
Fortin

(10) Patent No.: US 9,447,020 B2
(45) Date of Patent: Sep. 20, 2016

(54) POLYUNSATURATED FATTY ACID MONOGLYCERIDES, DERIVATIVES, AND USES THEREOF

(71) Applicant: SCF PHARMA INC., Sainte-Luce (CA)

(72) Inventor: Samuel C. Fortin, Sainte-Luce (CA)

(73) Assignee: SCF PHARMA INC., Sainte-Luce (CA)

( * ) Notice: Subject to any disclaimer, the term of this patent is extended or adjusted under 35 U.S.C. 154(b) by 0 days.

(21) Appl. No.: 14/525,621

(22) Filed: Oct. 28, 2014

(65) Prior Publication Data
US 2015/0119591 A1    Apr. 30, 2015

Related U.S. Application Data

(60) Provisional application No. 61/898,403, filed on Oct. 31, 2013.

(51) Int. Cl.
*C07C 59/00*      (2006.01)
*C07C 69/732*    (2006.01)
(Continued)

(52) U.S. Cl.
CPC ........... *C07C 69/732* (2013.01); *C07D 303/16* (2013.01)

(58) Field of Classification Search
CPC .... C07C 69/732; C07C 59/00; C07D 303/16
USPC .......................................... 549/561; 554/219
See application file for complete search history.

(56) References Cited

U.S. PATENT DOCUMENTS 6,180,671 B1    1/2001    Freedman et al.
6,552,081 B1    4/2003    Freedman et al.
(Continued)

FOREIGN PATENT DOCUMENTS

EP    1352648    10/2003
WO    02064166    8/2002
(Continued)

OTHER PUBLICATIONS

An English abstract of JP2000044588. Yagi et al. Novel monoacylglycosyl monoacylglycerols for surfactants. (Agency of Industrial Sciences and Technology, Japan) Jpn. Kokai Tokkyo Koho (2000), 7 pp. CODEN.
(Continued)

*Primary Examiner* — T. Victor Oh
(74) *Attorney, Agent, or Firm* — Bereskin & Parr LLP/S.E.N.C.R.L., s.r.l.

(57) ABSTRACT

There are provided compounds of formula (I):

wherein $X_1$ is O, NH, or S; $X_2$ is O, NH, or S; and $X_3$ is O, NH, or S;
and wherein R, $R_1$, $T_1$ and $T_2$ can represent various entities.
Such compounds can be useful, for example, for preventing, palliating or treating various diseases such as heart diseases, respiratory diseases, treating inflammatory abnormalities, metabolic disorders or diabetes.

13 Claims, 3 Drawing Sheets

(51) Int. Cl.
C07D 303/16 (2006.01)
C07D 303/12 (2006.01)

(56) References Cited

U.S. PATENT DOCUMENTS

| | | | |
|---|---|---|---|
| 7,138,431 | B1 | 11/2006 | Chilton |
| 7,981,915 | B2 | 7/2011 | Freedman |
| 8,119,690 | B2 * | 2/2012 | Fortin .................. C07C 69/587 514/549 |
| 8,198,324 | B2 | 6/2012 | Fortin |
| 8,222,295 | B2 | 7/2012 | Fortin |
| 8,329,747 | B2 | 12/2012 | Fortin |
| 8,722,737 | B2 | 5/2014 | Fortin |
| 2002/0188024 | A1 | 12/2002 | Chilton et al. |
| 2004/0214799 | A1 | 10/2004 | Mukai et al. |
| 2006/0121583 | A1 | 6/2006 | Lassalle et al. |
| 2009/0291102 | A1 | 11/2009 | Fortin |
| 2009/0292019 | A1 | 11/2009 | Fortin |
| 2010/0160261 | A1 | 6/2010 | Fortin |
| 2010/0196496 | A1 | 8/2010 | Fortin |
| 2012/0213872 | A1 | 8/2012 | Fortin |
| 2012/0251582 | A1 | 10/2012 | Fortin |
| 2013/0059911 | A1 | 3/2013 | Fortin |

FOREIGN PATENT DOCUMENTS

| | | |
|---|---|---|
| WO | 02089787 | 11/2002 |
| WO | 02096408 | 12/2002 |
| WO | 04000333 | 12/2003 |
| WO | 2004024136 | 3/2004 |
| WO | 2004064716 | 8/2004 |
| WO | 2006117668 | 11/2006 |
| WO | 2008036353 | 3/2008 |

OTHER PUBLICATIONS

An English abstract of JP149786 of Yazama et al., "Glyceroglycolipid and Carcinogenic Promoter Inhibitor", published on Jun. 13, 1995.

An English Abstract of JP 02131418 of Okazaki et al., "Comparison of Enhanced and Routine Methods for Measuring Ambient Low-Level Sulfur Dioxide", (Sansei Pharmaceutical Co., Ltd., Japan.) Jpn. Kokai Tokkyo Koho (1980), 7 pp.

An abstract of Myrdal et al., "Solubilization of Drugs in Aqueous Media" Department of pharmacy Practice and Science, College of Pharmacy, The University of Arizona, Encyclopedia of pharmaceutical technology, published on Oct. 2, 2006.

An abstract of Rohan et al., "Dietary factors and survival from breast cancer", National Cancer Institute of Canada (NCIC) Epidemiology Unit, University of Toronto, Nutr Cancer 1993,20(2) 167-77.

Kafrawy et al., "Docosahexaenoic acid in phosphatidylcholine mediates cytotoxacity more effectively than other ω-3 and ω-6 fatty acids", Department of Biology, Indiana University, Cancer Letters 132(1998) 23-29.

Aggarwal et al., Chapter 10, Curcumin-Biologican and medicinal Properties, 2007, Medicinal and Aromatic Plants—Industrial Profiles, Turmeric, 45, 297-368.

Kawashima et al., "Inhibition of Rat Liver Microsomal Desaturases by Curcumin and Related Compounds", Biosci. Biotech. Biochem., 60(1), pp. 108-110, 1996.

Shimizu et al., "Sesamin is a Potent and Specific Inhibitor of Δ5 Desaturase in Polyunsaturated Fatty Acid Biosynthesis", LIPIDS, vol. 26, No. 7, pp. 512-516, 1991.

Nakano et al., "Inhibitory Effects of Capsaicinoids on Fatty Acid Desaturation in a Rat Liver Cell Line", Biosci. Biotech. Biochem., 65(8), pp. 1859-1863, 2001.

Kawashima et al., "Nicardipine and Nifedipine Inhibit Fatty Acid Desaturases in Rat Liver Microsomes", Biosci. Biotech. Biochem., 60(10), pp. 1672-1676, 1996.

Kawashima et al., "Inhibitory effects of alkyl gallate and its derivatives on fatty acid desaturation", Biochimica et Biophysica Acta 1299, pp. 34-38, 1996.

Chau et al., "Monoglyceride and diglyceride lipases from human platelet microsomes", Biochimica et Biophysical Acta, 963, pp. 436-444, 1998.

Beharry et al., "Long-term docosahexaenoic acid therapy in a congenic murine model of cystic fibrosis", Am J Physiol Gastrointest Liver Physiol 292:G839-G848, Nov. 9, 2006.

C. R. Martin et al., "The safety and efficacy of oral docosahexaenoic acid supplementation for the treatment of primary sclerosing cholangitis—a pilot study", Aliment Pharmacol Ther, Nov. 30, 2011; 35: 255-265.

Freedman et al., "Fatty acids in cystic fibrosis", Curr Opin Pulm Med 2000, 6:530-532.

Monks, A., "Feasibility of a High-Flux Anticancer Drug Screen Using a Diverse Panel of Cultured Human Tumor Cell Lines", J Natl Cancer Inst, Jun. 5, 1991, 757-766, vol. 83, No. 11.

Rubinstein, L.V., "Comparison of In Vitro Anticancer-Drug Screening Data Generated with a Tetrazolium Assay Versus a Protein Assay Against a Diverse Panel of Human Tumor Cell Lines", J Natl Cancer Inst, Jul. 4, 1990, 1113-1118, vol. 82, No. 13.

Skehan, P., "New Colorimetric Cytotoxicity Assay for Anticancer-Drug Screening". J Natl Cancer Inst, Jul. 4, 1990, 1107-1112, vol. 82, No. 13.

Rose, D.P., "Omega-3 fatty acids as cancer chemopreventive agents", Phamarcology & Therapeutics, 1999, 217-244, 83.

Ohta et al., "Action of a New Mammalian DNA Polymerase Inhibitor, Sulfoquinovosyldiacylglycerol", Biol. Pharm. Bull., 1999, 111-116 22(2).

Pacetti et al., "High performance liquid chromatography-tandem mass spectrometry of phospholipid molecular species in eggs from hens fed diets enriched in seal blubber oil". Journal of Chromatography A, 2005, 66-73, 1097.

Schaaf et al., "Polyunsaturated monoglycerides and a pregnadiene in defensive glands of the water beetle *Agabus affinis*". Department of Animal Ecology II, Lipids (2000), 35(5), 543-550.

Vandevoorde et al. Influence of the degree of unsaturation of the acyl side chain upon the interaction of 1-analogues of 1-arachidonoylglycerol with monoacyglycerol lipase abd fatty acid amide hydrolase. Department of Pharmacology and Clinical Neuroscience, Umea University, Umea, Swed. Biochemical and Biophysical Research Communications (2005), 337(1), 104-109. Publisher: Elsevier.

Akoh, Casimir C., Lipase-catalyzed synthesis of partial glyceride. Dep. Food Sci. Technol., Univ. Georgia, Athens, GA, USA. Biotechnoloy Letters (1993), 15(9), 949-954.

Rosu et al., "Enzymic synthesis of glycerides from DHA-enriched PUFA ethyl ester by glycerolysis under vacuum". Graduate school of Bio- and Agro-Sciences, Laboratory of Molecular Biotechnology, Nagoya University, Nagoya Japan. Journal of Molecular Catalysis B. Enzymatic (1988), 4(4), 191-198.

Yamane et al. "Mutiple intensified performance of an enzyme-catalyzed reaction in organic medium". Laboratory of Molecular Biotechnology Graduates School of Bio- and Agro-Sciences, Nagoya University, Nagoya, Japan. Annals of the New York Academy of Sciences (1988), 864 (Enzyme Engineering XIV), 171-179.

Ando et al., "Reinvestigation of positional distribution of fatty acids in docosahexaenoic acid-rich fish oil triacyl-sn-glycerols". Department of Marine Bioresources Chemnistry, Faculty of Fisheries, Hokkaido Universit, Hakodate, Japan. Lipids (2000), 35(5), 579-582.

Kawashima et al., "Enzymatic synthesis of high-purity structured lipids with caprylic acid at 1,3-positions and polyunsaturated fatty acid at 2-positin". Sonoda Wowen's Junior College, Hyogo, Japan. Journal of the American Oil Chemists' Society (2001) 78(6), 611-616.

(56) References Cited

OTHER PUBLICATIONS

Watanabe et al. "n-3 Polyunsaturated fatty acid (PUFA) deficiency elevates and n-3 PUFA enrichment reduces brain 2-arachidonoyglycerol level in mice" Institute of Natural Medicine, Department of Clinical Application, Toyama Medical and Pharmaceutical University, Toyama, Japan. Prostaglandins Leukotrienes and Essential Fatty Acids (2003), 69(1), 51-59.

Watanabe et al., "Chemical signals involved in larval metamorphosis in Hydroides Ezoensis (Serpulidae; Polychaeta). Part II: isolation and identification of a new monoacyl Glycerol from adult tube clumps as a metamorphosis-including substance". Department of Applied Biological Chemistry, Faculty of Agricultur, Shizuoka University, Shizuoka, Japan. Journal of Marine Biotechnology (1998), 61(1), 11-15.

A partial English translation of Tanaka et al., Preparative separation of acylglycerol by cebtrifugal partition chromatography (CPC). Tsukuba Res. Lab., Nippon Oil and Fats Co., Ltd., Tsukuba, Japan. Yukagaku (1992), 41(1), 23-7.

Feng Li et al., "Biosynthesis of Docosahexaenoate-Containing Glycerolipid Molecular Species in the Retina" Journal of Molecular Neuroscience (2001), vol. 16, 206-214.

Zerouga et al., "Synthesis of a Novel Phosphatidylcholine Conjugated to Docosahexaenoic Acid and Methotrexate that Inhibits Cell Proliferation" Anti-Cancer Drugs (2002), 13, pp. 301-311.

* cited by examiner

POLYUNSATURATED FATTY ACID MONOGLYCERIDES, DERIVATIVES, AND USES THEREOF

CROSS-REFERENCE TO RELATED APPLICATIONS

The present application claims priority on U.S. 61/898,403 filed on Oct. 31, 2013, that is hereby incorporated by reference in its entirety.

FIELD OF THE DISCLOSURE

The present document relates to the field of medicinal chemistry. More particularly it relates to the field of active agents used as prevention and treatment of cancer, heart disease, respiratory diseases, inflammatory abnormalities, metabolic disorder, diabetes and hypertension.

BACKGROUND OF THE DISCLOSURE

An estimated 177,800 new cases of cancer (excluding about 74,100 non-melanoma skin cancers) and 75,000 deaths will occur in Canada in 2011. In 2007, cancer surpassed cardiovascular disease (heart and cerebrovascular) as the leading cause of death in Canada. In 2011, approximately 84,800 Canadian women will be diagnosed with cancer, and an estimated 35,100 women will die of cancer. Approximately 93,000 Canadian men will be diagnosed with cancer, and an estimated 39,900 men will die of cancer. On average, 487 Canadians will be diagnosed with cancer every day. (Canadian cancer society, 2011).

Lung, prostate, breast and colorectal cancer are the 4 most common cancer types in Canada and account for over 50% of all new cancer cases. Based on 2011 estimates: 40% of Canadian women and 45% of men will develop cancer during their lifetimes and an estimated 1 out of every 4 Canadians is expected to die from cancer. (Canadian cancer society, 2011).

Every 7 minutes in Canada, someone dies from heart disease or stroke. Heart disease and stroke are two of the three leading causes of death in Canada. In 2006 cardiovascular disease accounted for 30% of all deaths in Canada (69,019 deaths); 30% of all male deaths and 31% of all female deaths. (Hearth & Stroke Foundation of Canada, 2011)

Over 3 million Canadians cope with one of five serious respiratory diseases—asthma, chronic obstructive pulmonary disease (COPD), lung cancer, tuberculosis (TB), and cystic fibrosis. Canada is facing a wave of chronic respiratory diseases. Since many of these diseases can be tied to an aging population, the number of people with respiratory diseases can be expected to increase. The corresponding increase in demand for services will pose a significant challenge for the health care system. (Public Health Agency of Canada, 2011)

Inflammatory abnormalities are a large group of disorders which underlie a vast variety of human diseases including cancer heart disease Respiratory disease, arthritis, neurodegenerative disease like Alzheimer's disease, Parkinson's disease, Huntington's disease, Amyotrophic lateral sclerosis (ALS) and many more.

Therefore, there is a significant need in the art for novel compounds and methods that are useful for the prevention or treatment of aforementioned diseases with reduced or without side effects.

SUMMARY OF THE DISCLOSURE

According to one aspect there are provided compounds of formula (I):

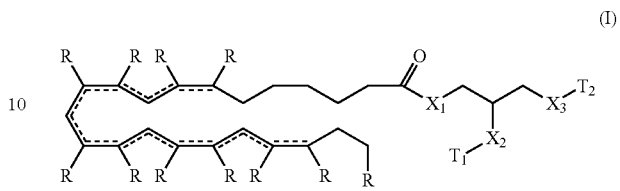

wherein
$X_1$ is O, NH, or S;
$X_2$ is O, NH, or S;
$X_3$ is O, NH, or S;
each R independently represents —H, —OH, —OR$_1$, —OOH, =O, =NR$_1$, =S, —OC(O)R$_1$, —OC(O)OR$_1$, —OC(O)NH$_2$, —OP(O)(OR$_1$)$_2$, —OS(=O)OR$_1$, —OS(=O)$_2$OR$_1$, —OS(=O)NH$_2$, —OS(=O)$_2$NH$_2$, —NH$_2$, —NHR$_1$, or —NHC(O)R$_1$, wherein at least one of the R is different than —H;
or at least two R are joined together so as to form a three- to seven-membered heterocycle comprising at least one heteroatom chosen from N, O and S;
$T_1$ and $T_2$ each independently represents —H, —C(=O)CH$_3$, —C(O)NH$_2$, —S(=O)OR$_1$, —S(=O)$_2$OR$_1$, —S(=O)$_2$NH$_2$, —P(=O)(OR$_1$)$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl; and
$R_1$ is H, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, —C3-C22 alkynyl, cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22(aryl)alkynyl, a sugar, or a sugar phosphate;
or a pharmaceutically acceptable salt thereof.

According to another aspect there are provided compounds of formulas (II), (III), (IV), (V), (VI), (VII), (VIII), (IX) or (X):

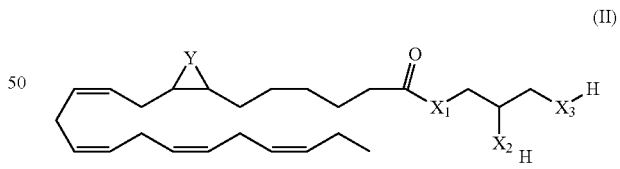

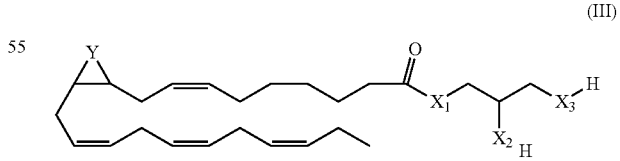

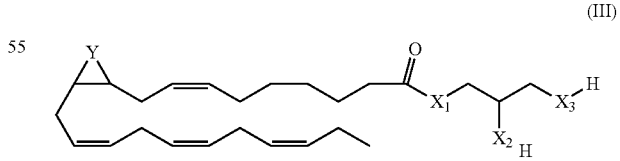

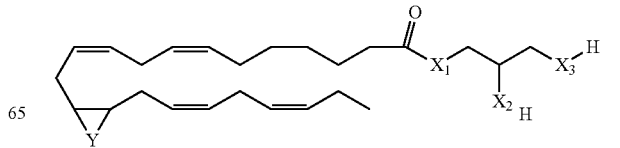

(V)
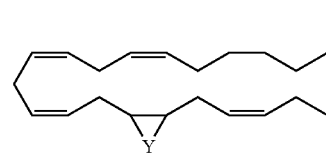

(VI)
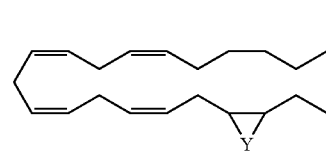

(VII)
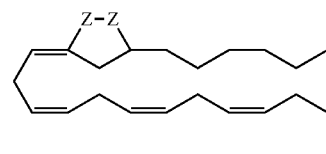

(VIII)
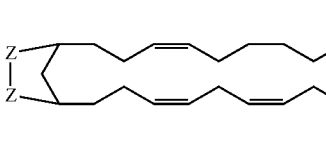

(IX)
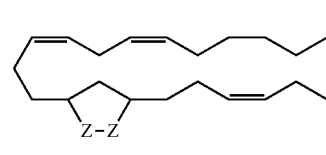

(X)
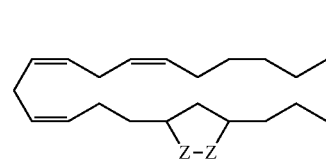

$X_1$ is O, NH, or S;
$X_2$ is O, NH, or S;
$X_3$ is O, NH, or S;
Y is O, NH, $NR_1$, $NC(O)R_1$ or S; and
$R_1$ is H, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, —C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22(aryl)alkynyl, a sugar, or a sugar phosphate;
or a pharmaceutically acceptable salt thereof.

According to another aspect there are provided compounds of formulas (XI), (XII), (XIII), (XIV), (XV), (XVI), (XVII), (XVIII) or (XIX):

(XI)
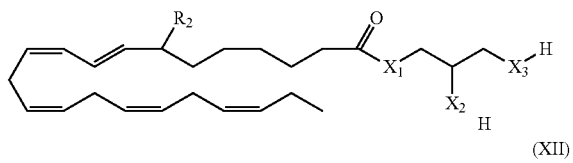

(XII)
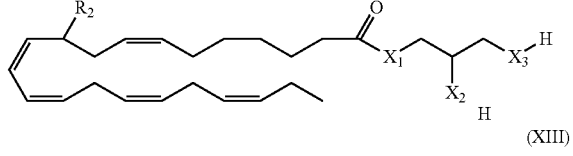

(XIII)
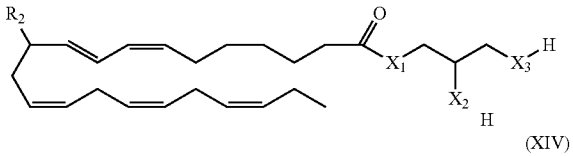

(XIV)
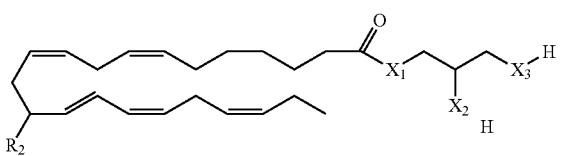

(XV)
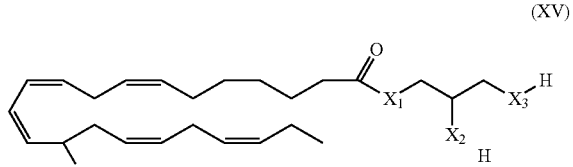

(XVI)
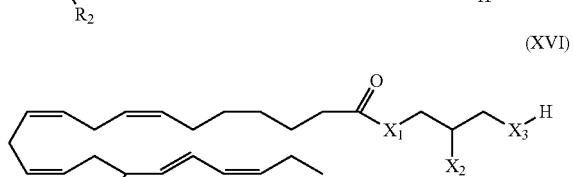

(XVII)
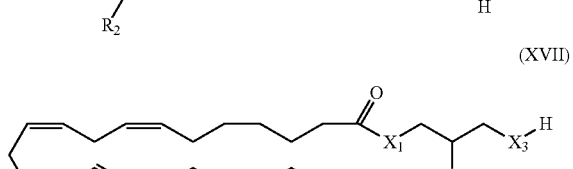

(XVIII)
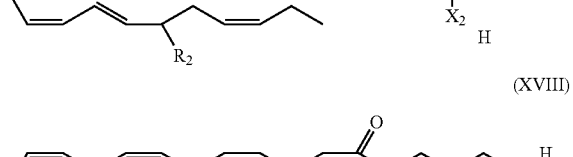

(XIX)
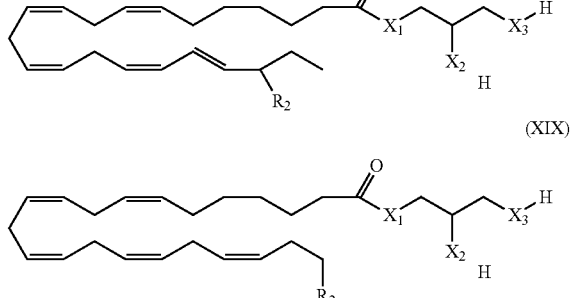

wherein
$X_1$ is O, NH, or S;
$X_2$ is O, NH, or S;

X₃ is O, NH, or S;

R₂ represents —OH, —OR₁, —OOH, =O, =NR₁, =S, —OC(O)R₁, —OC(O)OR₁, —OC(O)NH₂, —OP(O)(OR₁)₂, —OS(=O)OR₁, —OS(=O)₂OR₁, —OS(=O)NH₂, —OS(=O)₂NH₂, —NH₂, —NHR₁, or —NHC(O)R₁; and R₁ is H, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, —C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22(aryl)alkynyl, a sugar, or a sugar phosphate;

or a pharmaceutically acceptable salt thereof

According to another aspect there are provided compounds of formulas (XX), (XXI), (XXII), (XXIII), (XXIV), (XXV), (XXVI), (XXVII), (XXVIII), (XXIX), (XXX), (XXXI), (XXXVIII) or (XXXIX):

(XX)

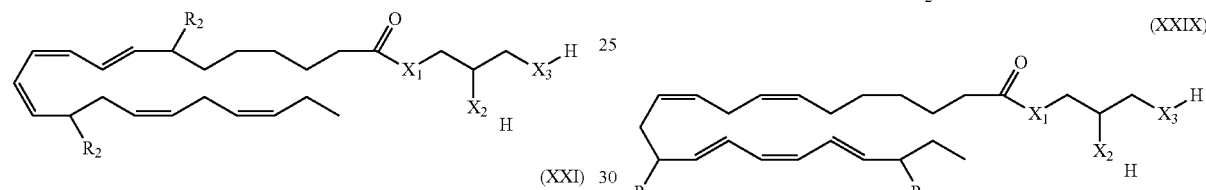

(XXI)

(XXII)

(XXIII)

(XXIV)

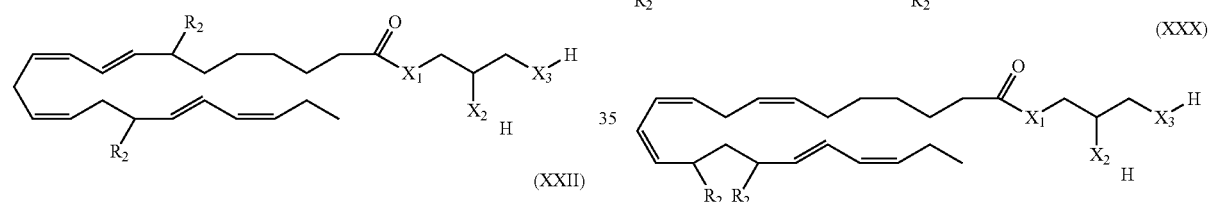

(XXV)

(XXVI)

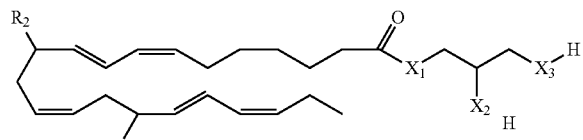

(XXVII)

(XXVIII)

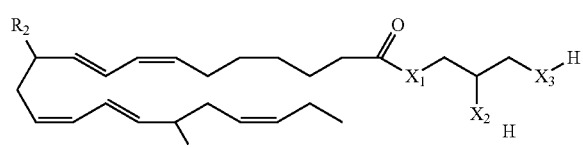

(XXIX)

(XXX)

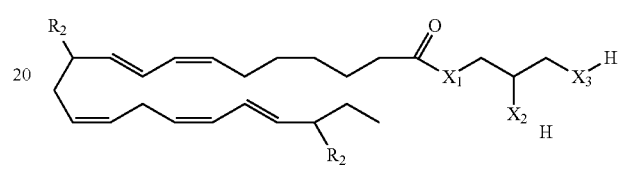

(XXXI)

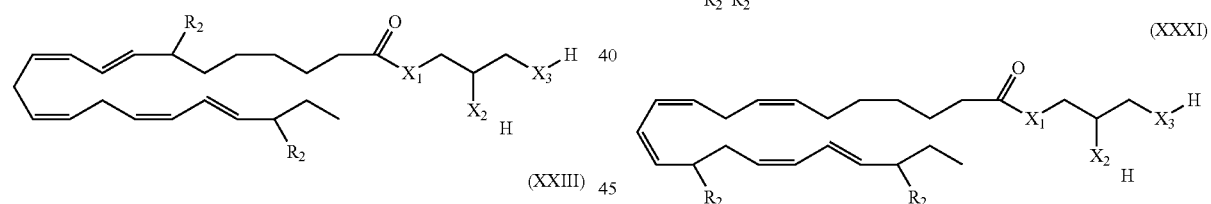

(XXXVIII)

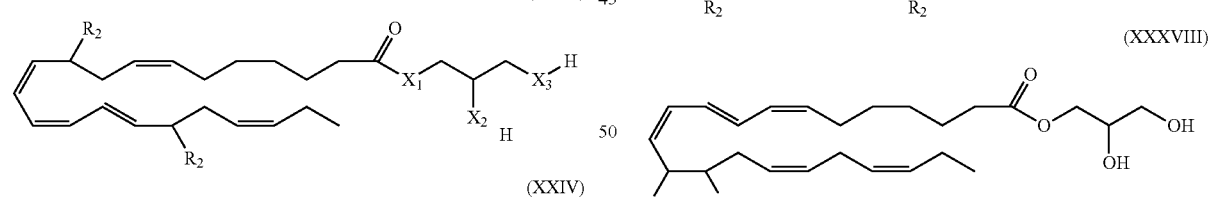

(XXXIX)

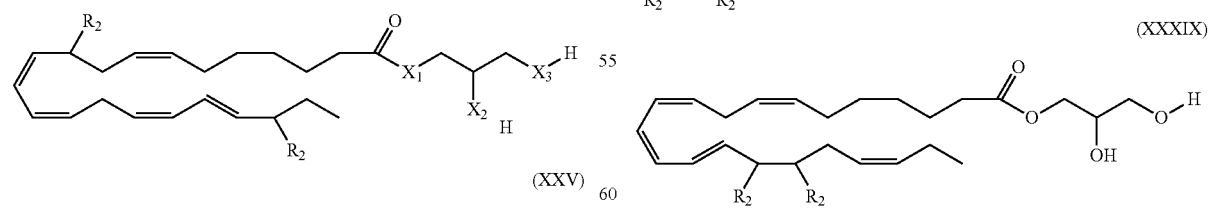

wherein
X₁ is O, NH, or S;
X₂ is O, NH, or S;
X₃ is O, NH, or S;

each $R_2$ independently represents —OH, —OR$_1$, —OOH, =O, =NR$_1$, =S, —OC(O)R$_1$, —OC(O)OR$_1$, —OC(O)NH$_2$, —OP(O)(OR$_1$)$_2$, —OS(=O)OR$_1$, —OS(=O)$_2$OR$_1$, —OS(=O)NH$_2$, —OS(=O)$_2$NH$_2$, —NH$_2$, —NHR$_1$, or —NHC(O)R$_1$; and $R_1$ is H, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, —C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22(aryl)alkynyl, a sugar, or a sugar phosphate;

or a pharmaceutically acceptable salt thereof.

According to another aspect there are provided compounds of formulas (XXXII), (XXXIII), (XXXIV), (XXXV), (XXXVI), (XL) or (XLI):

(XXXII)

(XXXIII)

(XXXIV)

(XXXV)

(XXXVI)

(XL)

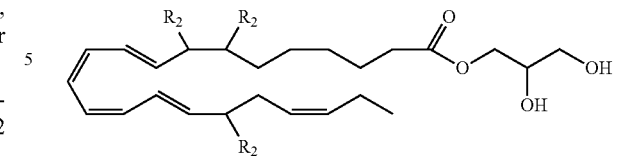

(XLI)

wherein
$X_1$ is O, NH, or S;
$X_2$ is O, NH, or S;
$X_3$ is O, NH, or S;
each $R_2$ independently represents —OH, —OR$_1$, —OOH, =O, =NR$_1$, =S, —OC(O)R$_1$, —OC(O)OR$_1$, —OC(O)NH$_2$, —OP(O)(OR$_1$)$_2$, —OS(=O)OR$_1$, —OS(=O)$_2$OR$_1$, —OS(=O)NH$_2$, —OS(=O)$_2$NH$_2$, —NH$_2$, —NHR$_1$, or —NHC(O)R$_1$; and $R_1$ is H, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, —C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22(aryl)alkynyl, a sugar, or a sugar phosphate;

or a pharmaceutically acceptable salts thereof.

According to another aspect, there is provided a composition comprising at least two compounds as defined in the present disclosure.

According to another aspect, there is provided a composition comprising at least one compound as defined in the present disclosure and a pharmaceutically acceptable carrier.

It was found that such compounds and compositions can be used so as to reduce or inhibit tumor growth, or inhibit tumor cell proliferation in vitro as well as in vivo. It was also found that the compounds previously mentioned can be useful as cancer chemopreventive agents (for example breast cancer, prostate cancer, colon cancer and lung cancer). The compounds of the present disclosure can be used separately or in a mixture of at least two of them (for example 2, 3 or 4 of them). The compounds can also be in isolated form. The compounds of the present disclosure can be used as a composition which also includes a pharmaceutically acceptable carrier.

BRIEF DESCRIPTION OF THE FIGURES

Further features and advantages of the disclosure will become more readily apparent from the following description of specific embodiments as illustrated by way of examples in the appended figures wherein.

DETAILED DESCRIPTION OF THE DISCLOSURE

Figure 1:
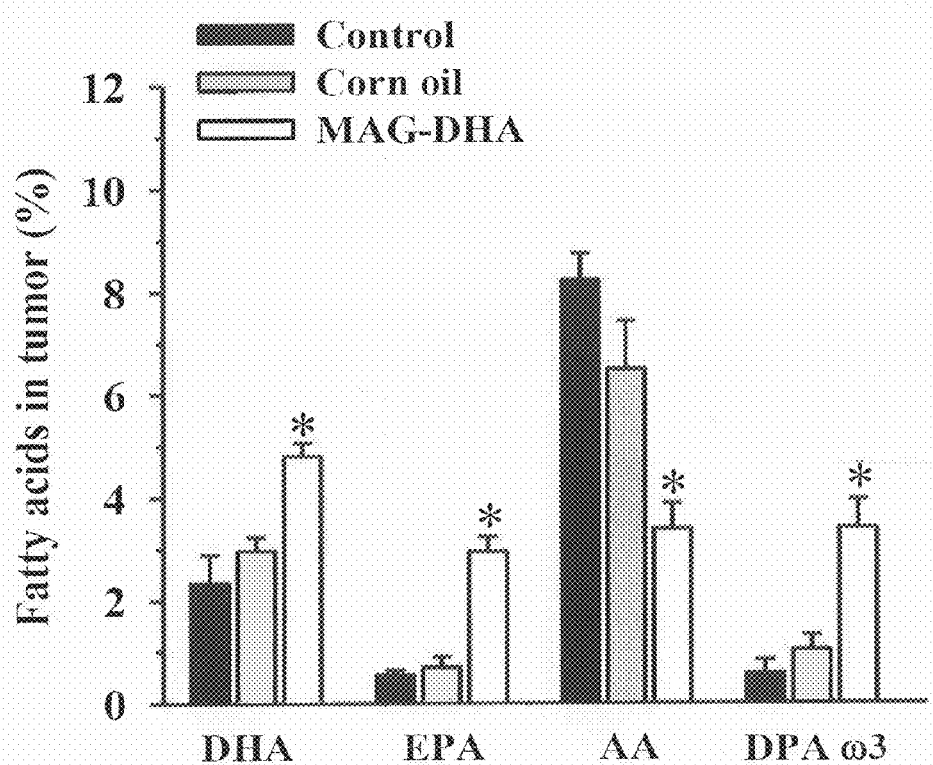
FIG. 1 is a diagram showing the results of an in vivo xenograph assay of DHA-monoglyceride, wherein the assay was carried out on A549 human cancer cell line.

Further features and advantages of the previously-mentioned compounds will become more readily apparent from the following description of non-limiting examples.

For example, in the compounds of formula (I), $X_1$, $X_2$ and $X_3$ can be O, $T_1$ and $T_2$ can be H and at least one R can be OH.

For example, in the compounds of formula (I), $X_1$, $X_2$ and $X_3$ can be NH, $T_1$ and $T_2$ can be H and at least one R can be OH.

For example, in the compounds of formula (I), $X_1$, $X_2$ and $X_3$ can be O, $T_1$ and $T_2$ can be H and at least one R can be OOH.

For example, in the compounds of formula (I), $X_1$, $X_2$ and $X_3$ can be NH, $T_1$ and $T_2$ can be H and at least one R can be OOH.

For example, in the compounds of formulas (II) to (VI), $X_1$, $X_2$ and $X_3$ can be O, and Y can be O.

For example, in the compounds of formulas (II) to (VI), $X_1$, $X_2$ and $X_3$ can be NH, and Y can be O.

For example, in the compounds of formulas (II) to (VI), $X_1$, $X_2$ and $X_3$ can be O, and Y can be NH.

For example, in the compounds of formulas (II) to (VI), $X_1$, $X_2$ and $X_3$ can be NH, and Y can be NH.

For example, in the compounds of formulas (VII) to (X), $X_1$, $X_2$ and $X_3$ can be O, and Z—Z can be O—O.

For example, in the compounds of formulas (VII) to (X), $X_1$, $X_2$ and $X_3$ can be NH, and Z—Z can be O—O.

For example, in the compounds of formulas (VII) to (X), $X_1$, $X_2$ and $X_3$ can be O, and Z—Z can be NH—NH.

For example, in the compounds of formulas (VII) to (X), $X_1$, $X_2$ and $X_3$ can be NH, and Z—Z can be NH—NH.

It was also found that the compounds and compositions of the present disclosure can provide effective pharmaceutical compositions for chemoprevention of cancer.

These compounds and compositions of the present disclosure can also be effective as radioenhancers for radiotherapy of cancer, or in combination with a pharmaceutically active ingredient in chemotherapy of cancer.

These compounds and compositions of the present disclosure can be effective for chemoprevention of various types of cancers (such as breast cancer, lung cancer, prostate cancer, colon cancer). Tumors growth of such types of cancer can be inhibited or reduces with these compounds.

These compounds and compositions of the present disclosure can also be effective as prevention or treatment of the following diseases: heart disease, respiratory diseases, inflammatory abnormalities, metabolic disorder, diabetes and hypertension. They can also be useful for palliating such diseases.

These compounds and compositions of the present disclosure can also be effective for reducing hypertension or blood triglycerides level.

According to another aspect there is provided a method for chemopreventing or palliating cancer comprising the step of administering to a subject at least one compound or at least one composition of the present disclosure.

According to another aspect there is provided a method for inhibiting tumor growth, inhibiting tumor cell proliferation, or reducing tumor growth, in vitro or in vivo, comprising contacting the tumor with a tumor growth reducing effective amount of at least one compound or at least one composition of the present disclosure.

According to another aspect there is provided a method of reducing tumor growth in a subject comprising administering to the subject at least one compound or at least one composition of the present disclosure.

According to another aspect there is provided a method for radioenhance the radiotherapy of cancer, or to enhance chemotherapy with a pharmaceutically active ingredient in chemotherapy of cancer in a subject comprising administering to the subject at least one compound or at least one composition of the present disclosure.

According to another aspect there is provided a method of reducing inflammatory abnormalities in a subject comprising administering to the subject at least one compound or at least one composition of the present disclosure.

According to another aspect there is provided a method of reducing hypertension in a subject comprising administering to the subject at least one compound or at least one composition of the present disclosure.

According to another aspect there is provided a method of reducing blood triglycerides level in a subject comprising administering to the subject at least one compound or at least one composition of the present disclosure.

According to another aspect there is provided a method for preventing, palliating or treating heart diseases comprising the step of administering to a subject at least one compound or at least one composition of the present disclosure.

For example, the heart diseases can be chosen from coronary artery disease, ischemic heart disease, cardiomyopathy, hypertensive heart disease, heart failure, pulmonary heart disease, cardiac dysrhythmias, inflammatory heart disease, endocarditis, inflammatory cardiomegaly, myocarditis, valvular heart disease, cerebrovascular disease, peripheral arterial disease, congenital heart disease and rheumatic heart disease.

According to another aspect there is provided a method for preventing, palliating or treating respiratory diseases comprising the step of administering to a subject at least one compound or at least one composition of the present disclosure.

For example, the respiratory diseases can be chosen from asthma, cystic fibrosis, emphysema, chronic obstructive pulmonary disorder or acute respiratory distress syndrome, small cell lung cancer, non-small cell lung cancer (adenocarcinoma of the lung, squamous cell carcinoma of the lung or large cell lung carcinoma), lymphoma, pulmonary embolism, pulmonary arterial hypertension, pulmonary edema, pulmonary hemorrhage and pulmonary inflammation.

According to another aspect there is provided a method for preventing, palliating or treating inflammatory abnormalities comprising the step of administering to a subject at least one compound or at least one composition of the present disclosure.

For example, the inflammatory abnormalities can be chosen from acne vulgaris, autoimmune diseases, autoinflammatory diseases, celiac disease, chronic prostatitis, glomerulonephritis, hypersensitivities, inflammatory bowel diseases, interstitial cystitis, pelvic inflammatory disease, reperfusion injury, rheumatoid arthritis, sarcoidosis, transplant rejection and vasculitis, According to another aspect there is provided a method for preventing, palliating or treating metabolic disorders comprising the step of administering to a subject at least one compound or at least one composition of the present disclosure.

For example, the metabolic disorders can be chosen from obesity, hyperthyroidism, hypothyroidism, diabetes, dyslipidemia, hypolipidemia, galactosemia and phenylketonuria.

According to another aspect there is provided a method for preventing, palliating or treating diabetes comprising the step of administering to a subject at least one compound or at least one composition of the present disclosure.

For example, the diabetes can be chosen from type I diabetes mellitus, Type II diabetes mellitus and gestational diabetes.

According to another aspect there is provided a method for preparing a compound of formula (I), as previously, the method comprising reacting a compound of formula (XXXVII)

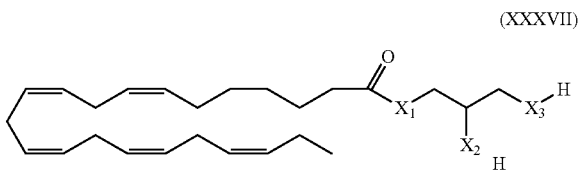

(XXXVII)

in which $X_1$, $X_2$ and $X_3$ are as previously defined, with an enzyme or catalyst in presence of an oxidant or an oxidant alone For example, a compound of formula (XXXVII) and oxygen can be reacted together in the presence of an enzyme for example a 15-lipoxygenase.

The enzyme can be chosen from lipoxygenase, cyclooxygenase, or cytochrome P450.

The oxidant can be oxygen, peroxide, ozone, peroxy-acid or organic peroxy-acid.

The three- to seven-membered membered heterocycle can be an aromatic heterocycle or a non-aromatic heterocycle.

The term "subject" as used herein includes all members of the animal kingdom including human. According to one embodiment, the subject is a human.

The expression a "therapeutically effective amount", "effective amount" or a "sufficient amount" of a compound or composition of the present disclosure is a quantity sufficient to, when administered to the subject, including a mammal, for example a human, effect beneficial or desired results, including clinical results, and, as such, an "effective amount" or synonym thereto depends upon the context in which it is being applied. For example, in the context of treating cancer, for example, it is an amount of the compound or composition sufficient to achieve such treatment of the cancer as compared to the response obtained without administration of the compound or composition. The amount of a given compound or composition of the present disclosure that will correspond to an effective amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a "therapeutically effective amount", "effective amount" or a "sufficient amount" of a compound or composition of the present disclosure is an amount which inhibits, suppresses or reduces a cancer (e.g., as determined by clinical symptoms or the amount of cancerous cells) in a subject as compared to a control.

The term "alkyl" as used herein means straight and/or branched chain, saturated alkyl groups.

The term "aryl" as used herein refers to a cyclic or polycyclic aromatic ring. For example the aryl group can be phenyl or napthyl.

The expression "aromatic heterocycle" as used herein refers to an aromatic cyclic or fused polycyclic ring system having at least one heteroatom selected from the group consisting of N, O, and S. Non-limitative examples include heteroaryl groups are furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

The expression "non-aromatic heterocycle" includes non-aromatic rings or ring systems that contain at least one ring having at least one hetero atom (such as nitrogen, oxygen or sulfur). This term includes, in a non-imitative manner all of the fully saturated and partially unsaturated derivatives of the above mentioned aromatic heterocycles groups. Examples of non-aromatic heterocycle groups include, in a non-limitative manner, pyrrolidinyl, tetrahydrofuranyl, morpholinyl, thiomorpholinyl, piperidinyl, piperazinyl, thiazolidinyl, isothiazolidinyl, and imidazolidinyl.

The expression "DPA" as used herein refers to all-cis-7,10,13,16,19-docosapentaenoic acid.

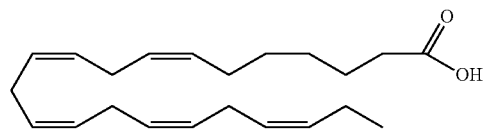 [SMILES: CC/C=C\C/C=C\C/C=C\C/C=C\C/C=C\CCCCCC(=O)O]

The expression "DHA" as used herein refers to all-cis-4,7,10,13,16,19-docosahexaenoic acid.

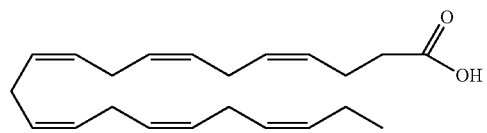 [SMILES: CC/C=C\C/C=C\C/C=C\C/C=C\C/C=C\C/C=C\CCC(=O)O]

The expression "EPA" as used herein refers to all-cis-5,8,11,14,17-eicosapentaenoic acid.

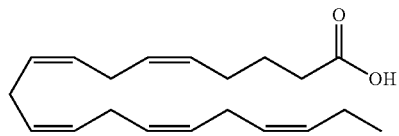 [SMILES: CC/C=C\C/C=C\C/C=C\C/C=C\C/C=C\CCCC(=O)O]

The expression "MAG-DPA" as used herein refers to sn1(3)-all-cis-7,10,13,16,19-docosapentaenoylglyceride and the synthesis of MAG-DPA from DPA is described in WO/2008/098375, hereby incorporated by reference in its entirety.

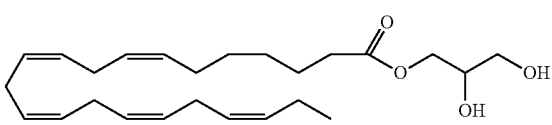

The expression "MAG-DHA" as used herein refers to sn1(3)-all-cis-4,7,10,13,16,19-docosahexaenoylglyceride and the synthesis of MAG-DHA from DHA is described in WO/2008/098375.

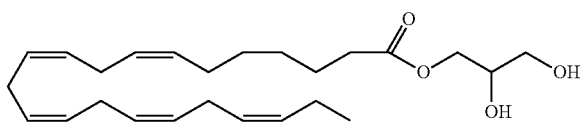 [SMILES: CC/C=C\C/C=C\C/C=C\C/C=C\C/C=C\CCCCCC(=O)OCC(O)CO]

The expression "MAG-EPA" as used herein refers to sn1(3)-all-cis-5,8,11,14,17-eicosapentaenoylglyceride and the synthesis of MAG-EPA from EPA is described in WO/2008/098375.

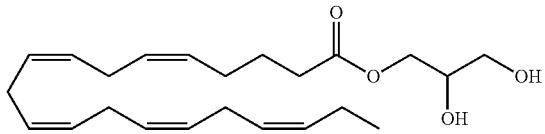

The expression "compound(s) and/or composition(s) of the present disclosure" as used in the present document refers to compounds of formulas (I) to (XXXVI) presented in the present disclosure, isomers thereof, such as stereoisomers (for example, enantiomers, diastereoisomers, including racemic mixtures) or tautomers, or to pharmaceutically acceptable salts, solvates, hydrates and/or prodrugs of these compounds, isomers of these latter compounds, or racemic mixtures of these latter compounds, and/or to composition(s) made with such compound(s) as previously indicated in the present disclosure. The expression "compound(s) of the present disclosure" also refers to mixtures of the various compounds or variants mentioned in the present paragraph.

It is to be clear that the present disclosure includes isomers, racemic mixtures, pharmaceutically acceptable salts, solvates, hydrates and prodrugs of compounds described therein and mixtures comprising two or more of such compounds.

The compounds of the disclosure may have at least one asymmetric centre. Where the compounds according to the present document possess more than one asymmetric centre, they may exist as diastereomers. It is to be understood that all such isomers and mixtures thereof in any proportion are encompassed within the scope of the present disclosure. It is to be understood that while the stereochemistry of the compounds of the present disclosure may be as provided for in any given compound listed herein, such compounds of the disclosure may also contain certain amounts (for example less than 30%, less than 20%, less than 10%, or less than 5%) of compounds of the present disclosure having alternate stereochemistry.

The expression "pharmaceutically acceptable" means compatible with the treatment of subjects such as animals or humans.

The expression "pharmaceutically acceptable salt" means an acid addition salt or basic addition salt which is suitable for or compatible with the treatment of subjects such as animals or humans.

The expression "pharmaceutically acceptable acid addition salt" as used herein means any non-toxic organic or inorganic salt of any compound of the present disclosure, or any of its intermediates. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds of the present disclosure are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of the compounds of the present disclosure, for laboratory use, or for subsequent conversion to a pharmaceutically acceptable acid addition salt. In embodiments of the present disclosure, the pharmaceutically acceptable acid addition salt is the hydrochloride salt.

The term "pharmaceutically acceptable basic addition salt" as used herein means any non-toxic organic or inorganic base addition salt of any acid compound of the invention, or any of its intermediates. Acidic compounds of the invention that may form a basic addition salt include, for example, where R is $CO_2H$. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art. Other non-pharmaceutically acceptable basic addition salts, may be used, for example, in the isolation of the compounds of the invention, for laboratory use, or for subsequent conversion to a pharmaceutically acceptable acid addition salt.

The formation of a desired compound salt is achieved using standard techniques. For example, the neutral compound is treated with an acid or base in a suitable solvent and the formed salt is isolated by filtration, extraction or any other suitable method.

The term "solvate" as used herein means a compound of the present disclosure, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds of the present disclosure will vary depending on the compound and the solvate. In general, solvates are formed by dissolving the compound in the appropriate solvent and isolating the solvate by cooling or using an antisolvent. The solvate is typically dried or azeotroped under ambient conditions.

The term "suitable" means that the selection of the particular group or conditions would depend on the specific synthetic manipulation to be performed and the identity of the molecule but the selection would be well within the skill of a person trained in the art. All process steps described herein are to be conducted under conditions suitable to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

Compounds of the present disclosure include prodrugs. In general, such prodrugs will be functional derivatives of these compounds which are readily convertible in vivo into the compound from which it is notionally derived. Prodrugs of the compounds of the present disclosure may be conventional esters formed with available hydroxy, or amino group. For example, an available OH or nitrogen in a compound of the present disclosure may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters. In certain instances, the prodrugs of the compounds of the present disclosure are those in which one or more of the hydroxy groups in the compounds is masked as groups which can be converted to hydroxy groups in vivo. Conventional procedures for the selection and preparation of suitable prodrugs are described, for example, in "Design of Prodrugs" ed. H. Bundgaard, Elsevier, 1985.

Compounds of the present disclosure include radiolabeled forms, for example, compounds labeled by incorporation within the structure $^2H$, $^3H$, $^{14}C$, $^{15}N$, or a radioactive halogen such as $^{125}I$. A radiolabeled compound of the compounds of the present disclosure may be prepared using standard methods known in the art.

As used herein, and as well understood in the art, "treatment" or "treating" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" or "treating" can also mean prolonging survival as compared to expected survival if not receiving treatment.

"Palliating" a disease or disorder, means that the extent and/or undesirable clinical manifestations of a disorder or a disease state are lessened and/or time course of the progression is slowed or lengthened, as compared to not treating the disorder.

The expression "derivative thereof" as used herein when referring to the compounds of the present disclosure means a derivative of the compounds of formulas (I) to (XLI) that has a similar biological activity and that could be used as an alternative to the compounds of formulas (I) to (XLI) in order to obtain the same desired result.

The expression "derivative thereof" as used herein when referring to a compound of formula (XXXVII) means a derivative of the compound of formula (XXXVII) that has a similar reactivity and that could be used as an alternative to the compound of formula (XXXVII) in order to obtain the same desired result i.e. formation of a compounds of formulas (I) to (XLI) when reacting this derivative with a reactant as described in the present disclosure in order to form such compounds of formulas (I) to (XLI).

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The sugar can be chosen from 5-carbon sugars and 6-carbon sugars. Non-limiting examples of 5-carbon sugar include ribose, arabinose, xylose, and lyxose. Non-limiting examples of 6-carbon sugar include glucose, galactose, mannose, allose, gulose, idose, talose, and altrose.

The sugar phosphate can be chosen from monosaccharides (such as mannose-6-phosphate, glucose-6-phosphate, galactose-6-phosphate, mannose-I-phosphate, glucose-I-phosphate and galactose-I-phosphate), disaccharides (such as 6-O-phosphoryl-a-D-mannopyranosyl-(1-2)-D-mannopyranose, 6-O-phosphoryl-a-D-mannopyranosyl-(1-3)-mannopyranose, 6-O-phosphoryl-a-D-mannopyranosyl-(1-6)-D-mannopyranose), trisaccharides (such as 6-O-phosphoryl-a-D-mannopyranosyl-(1-2)-D-mannopyranosyl-(I-2)-D-mannopyranose), and higher linear or branched oligosaccharides (such as pentamannose-6-phosphate).

For example, the subject can be a mammalian such as a human.

For example, the compounds of the present disclosure can be of formulas:

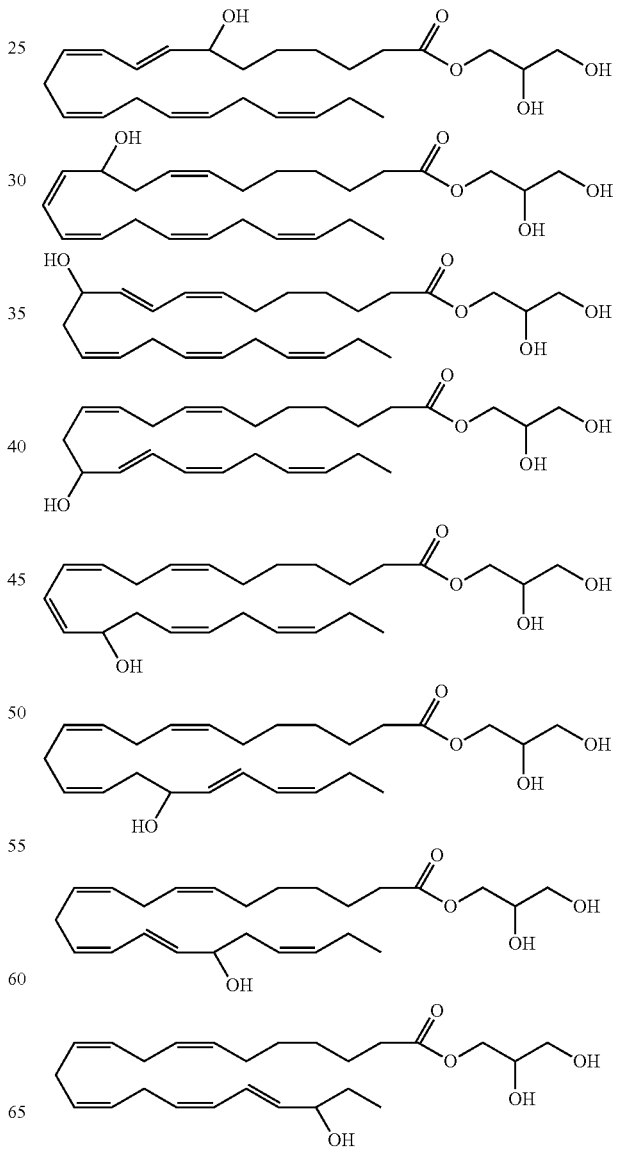

17
-continued
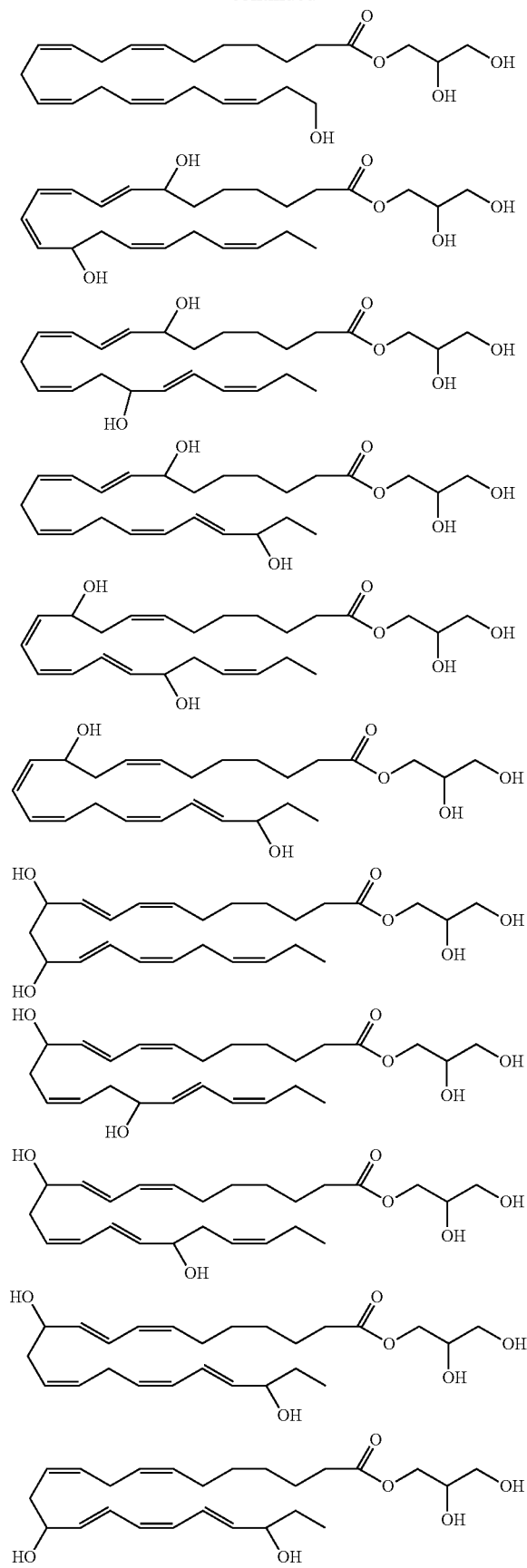
18
-continued
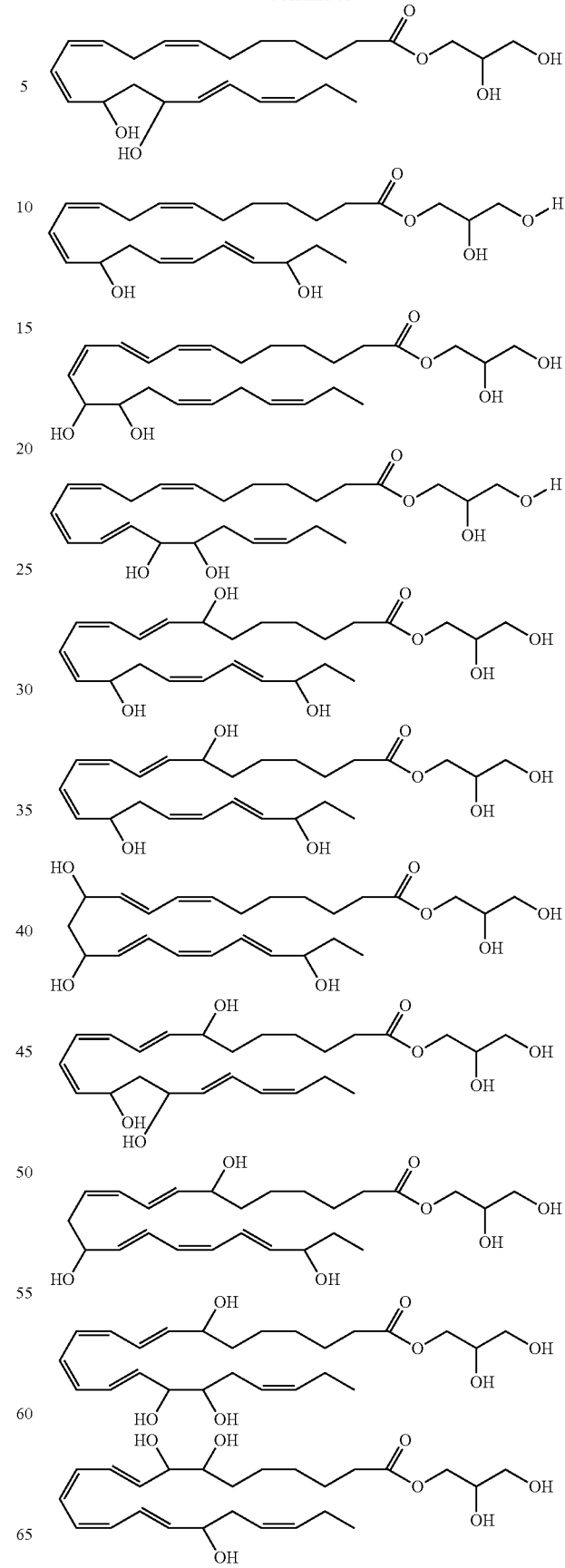

-continued

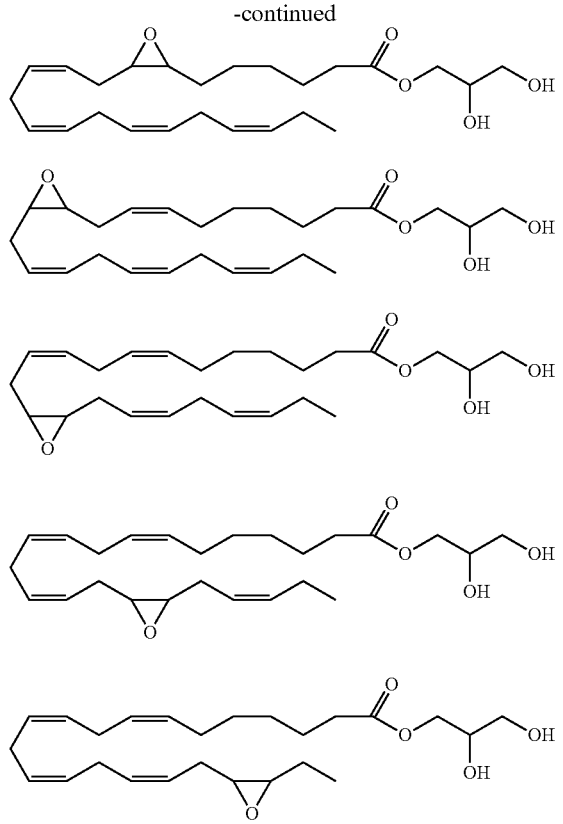

EXAMPLE 1

In vivo Tumor Xenograft Experiment.

Female CD-1 nude mice were obtained from Charles River Laboratories (Montreal, Qc, Canada). All studies involving mice were approved by the institutional animal care committee (Protocol: #237-10). Human A549 xenografts were established in 4-week-old female CD-1 nude mice. Mice were inoculated with 0.2 ml of a solution of 1×106 A549 cells subcutaneously on the right flank. Mice were randomly assigned into 3 groups, control (untreated), corn oil and MAG-DHA (CA2672513, CA2677670) treated (n=6 per group). Corn oil and MAG-DHA were administrated per os (618 mg/kg) daily following cell inoculation. Treatments were continued for 48 days. Mice were sacrificed when tumor volume reached ≈1.5 cm3 in the control group. Tumor tissues were harvested 24 hours after treatment completion. Tumor tissue fatty acids compositions were measured using a high-performance liquid chromatography (HPLC)-MS method [Gagne S and al. J Lipid Res 2007 January; 48(1):252-9] modified to detect complete fatty acid composition. Data were acquired in SIM mode corresponding to the following fatty acids: C20:4 (AA), C20:5 (EPA), C22:5 (DPA), C22:6 (DHA). The linear calibration curves were obtained in the concentration range of 2 to 500 µg/ml FIG. 1 represents the fatty acids compositions of tumors after MAG-DHA oral supplementation. The MAG-DHA group shows a significant increase in EPA, DHA and DPA when compared to control and corn oil groups. These results demonstrate that MAG-DHA is metabolically converted into EPA and DPA in human cancer cells.

EXAMPLE 2

Effect of MAG-DHA, MAG-EPA and MAG-DPA Treatments on Growth of SW620 Cells.

Human SW620 colorectal carcinoma cells were obtained from the American Type Culture Collection (ATCC) and maintained in Leitbovitz's L-15 medium containing 10% FBS, 10 mM HEPES, 2.2 g/L Na2C03 and 10 units/ml penicillin, 100 µg/ml streptomycin. Cells were grown in a 5% CO2 incubator at 37° C. A predefined number of SW620 cells were allowed to grow in 24 wells plates (1×104 cells/well) for 3 days until cells reached 80% confluence. Then, cells were starved in Leitbovitz's medium without FBS for 8 h. Then, the culture medium was replaced with Leitbovitz+0.2% FBS and different concentrations of MAG-DHA, MAG-EPA or MAG-DPA (0.1, 0.3, 1, 3, 10, 30 and 100 µM) were added to each well. Culture media were changed every 24 h and cells were treated for 48 h. After 48, the medium was removed from the culture plates and 0.05% trypsing EDTA was used to detach the cells from the surface of the culture plates. The harvested cells were counted, both the viable and dead ones, using a Countess Automated Cell Counter (Invitrogen Inc.). Briefly, for each condition an appropriated cell dilution was prepared from the harvested cells and an aliquot was mixed with an equal volume of 0.4% trypan blue, and 10 µl was transferred into each side of a Countess™ chamber slide. All concentrations tested were performed in triplicata and were representative of 5 independent experiment.

Figure 2:
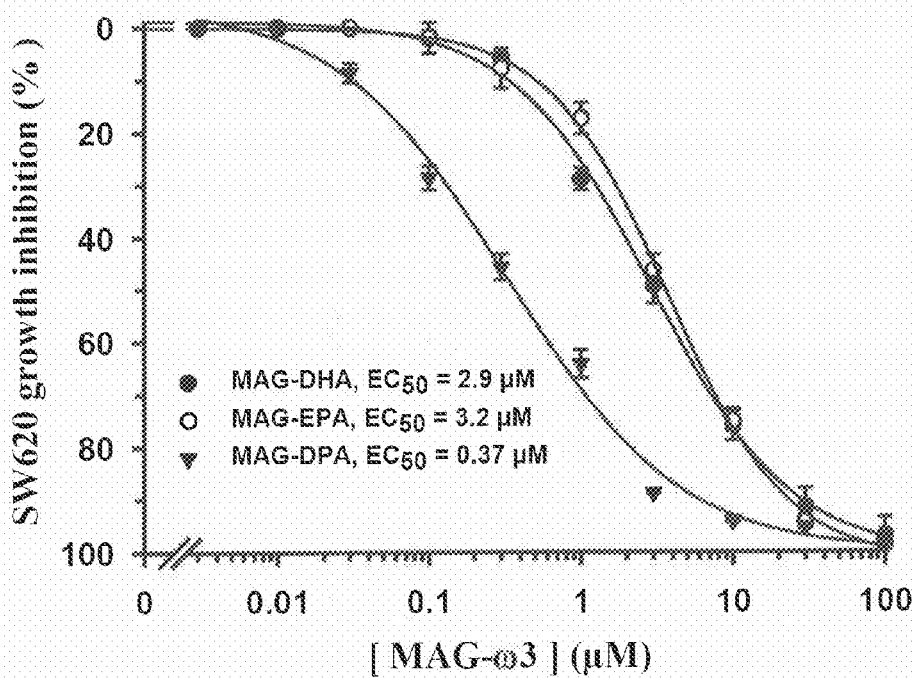
FIG. 2 is a diagram showing the results of an in vitro assay of EPA-monoglyceride, DHA-monoglyceride and DPA-monoglyceride, wherein the assay was carried out on SW620 human cancer cell line.

FIG. 2 represents an in vitro cumulative concentration response curves (CCRC) of MAG-DHA, MAG-EPA and MAG-DPA (0.01-100 µM) on SW620 cell growth. The $IC_{50}$ of MAG-DPA is 0.37 µM compared to 2.90 µM for MAG-DHA and 3.20 µM for MAG-EPA. This result clearly shows that MAG-DPA is ten (10) times more active than MAG-EPA or MAG-DHA. This result also suggest that DPA is responsible for the activity of the MAG-DHA because human cancer cells can convert DHA to DPA as shown in example 1.

EXAMPLE 3

Effect of MAG-DHA Treatment in the Presence of Luteolin on Apoptosis of SW620 Cells.

SW620 cells were cultured in 25 cm2 flask with Leitbovitz's medium in the presence of 10% FBS until cells reached 60% confluence. Then, cells were starved for 8 h in Leitbovitz medium without FBS. The culture medium was replaced with Leitbovitz+0.2% FBS and cells were untreated (Control) and treated with either 3 µM MAG-DHA or 3 µM MAG-DHA in the presence of 1 µM luteolin (a 15-lipoxygenase inhibitor). After 48 h, whole cell extracts were prepared from control and treated cells. The culture medium was removed from each culture flask and the cells were rinsed with ice-cold PBS. Then the PBS solution was removed and 0.5 ml of RIPA lysis buffer containing phosphatases and proteases inhibitor was added to each flask and incubated on ice for 15 min. The cell suspension was transferred to a eppendorf tube and was sonicated for 10 s. The tubes were centrifuged (14 000 rpm) for 10 min at 4° C. followed by aspiration of 99% of the supernatant. Protein concentrations in whole-cell extracts for control and treatments conditions were determined using the BCA protein assay kit according to manufacturer instructions.

Detection of Cleaved Caspase3, Caspase-3 Western Blotting: Briefly, 30 µg of total protein extract was separated in a 12% SDS-polyacrylamide gel and blotted onto a nitrocellulose membrane in 25 mmol/L Tris and 190 mmol/L glycin at 4° C. for 70 min at 80 V. Blots on nitrocellulose membrane were blocked in 5% milk, Tris-buffered saline (25 mmol/L Tris and 135 mmol/L NaCl; pH 7.6), and 0.1% Tween for 2 h and then incubated overnight with either rabbit anti-human cleaved caspases-3 or rabbit anti-human caspases-3 polyclonal antibodies. After washing the blot with Tris-buffered saline containing 0.1% Tween and incubating it with anti-rabbit IgG horseradish peroxidase-linked antibody (1:2000) at room temperature for 1 h, the blot was washed extensively, developed using ECL Western blotting substrate, and recorded on Kodak Biomax MR film. Following scanning of the blots, optical densities were quantified with Adobe Photoshop CS5.

Figure 3:
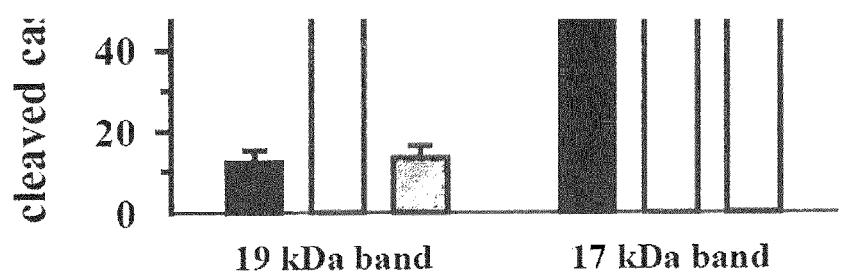
FIG. 3 is a diagram showing the results of an in vitro assay of DHA-monoglyceride in presence of luteolin, wherein the assay was carried out on SW620 human cancer cell line.

FIG. 3 represents an in vitro quantitative analysis of caspase-3 and cleaved caspase-3 in control, MAG-DHA and MAG-DHA+ luteolin treated SW620 cells. The caspases are a family of proteins that are one of the main executors of the apoptotic process. The caspase-3 has virtually no activity until it is cleaved by an initiator caspase after apoptotic signaling events. Cleaved caspase-3/caspase-3 ratio assay is a good indicator of apoptosis in cancer cells. Luteolin is one of the most potent commercially available 15-lipoxygenase inhibitor and lipoxygenase is a family of iron-containing enzymes that catalyse the dioxygenation of polyunsaturated fatty acids like EPA, DHA or DPA. Based on this result, a fatty acid oxidation process need to occur to induce apoptosis in human cancer cells.

As shown in the previous examples, MAG-DPA is more active than MAG-EPA or MAG-DHA. Cancer cells can convert one fatty acid to the other and an oxidation reaction need to occur to induce apoptosis. For these reasons it is believed, without wishing to being bound to such a theory, that compounds of formula (I) would likely be responsible for the activity of MAG-EPA, MAG-DHA and MAG-DPA.

EXAMPLE 4

Preparation of Compounds 2 and 3

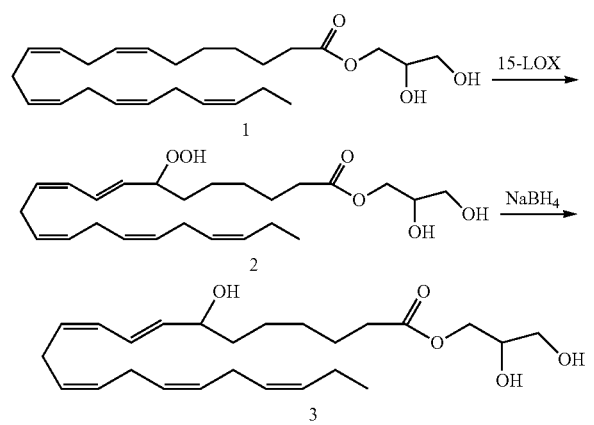

MAG-DPA (1) (0.1 mM) was prepared in borate buffer (50 mM, pH 12) from a stock solution (10 mM in ethanol), and the reaction initiated by the addition of soybean 15-lipoxygenase (2 mg added per 10 mL substrate solution). The reaction mixture was stirred for 15 min at room temperature, and then the hydroperoxides (2) were reduced by the addition of sodium borohydride (1 M, 0.2 mL added per 10 mL substrate solution). The solution was acidified by the drop-wise addition of glacial acetic acid (50 μL added per 10 mL substrate solution) after 15 minutes and left with gentle stirring until foaming stopped. Compound (3) was extracted by chloroform solvent extraction. No further purification was required.

EXAMPLE 5

Preparation of Compounds 4 and 5

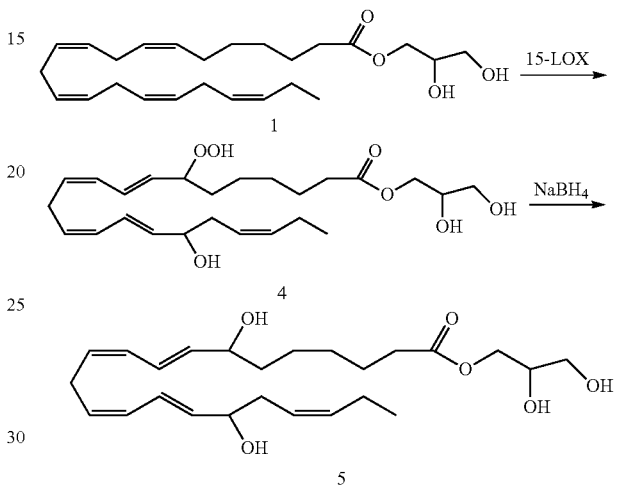

MAG-DPA (1) (0.1 mM) was prepared in borate buffer (50 mM, pH 9) from a stock solution (10 mM in ethanol), and the reaction initiated by the addition of soybean 15-lipoxygenase (5 mg added per 10 mL substrate solution). The reaction mixture was stirred for 15 min at room temperature, and then the dihydroperoxides (4) were reduced by the addition of sodium borohydride (1 M, 0.2 mL added per 10 mL substrate solution). The solution was acidified by the drop-wise addition of glacial acetic acid (50 μL added per 10 mL substrate solution) after 15 minutes and left with gentle stirring until foaming stopped. Compound (5) was extracted by chloroform solvent extraction. No further purification was required.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth, and as follows in the scope of the appended claims.

What is claimed is:
1. A compound of formula:

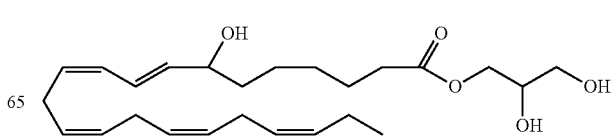

-continued
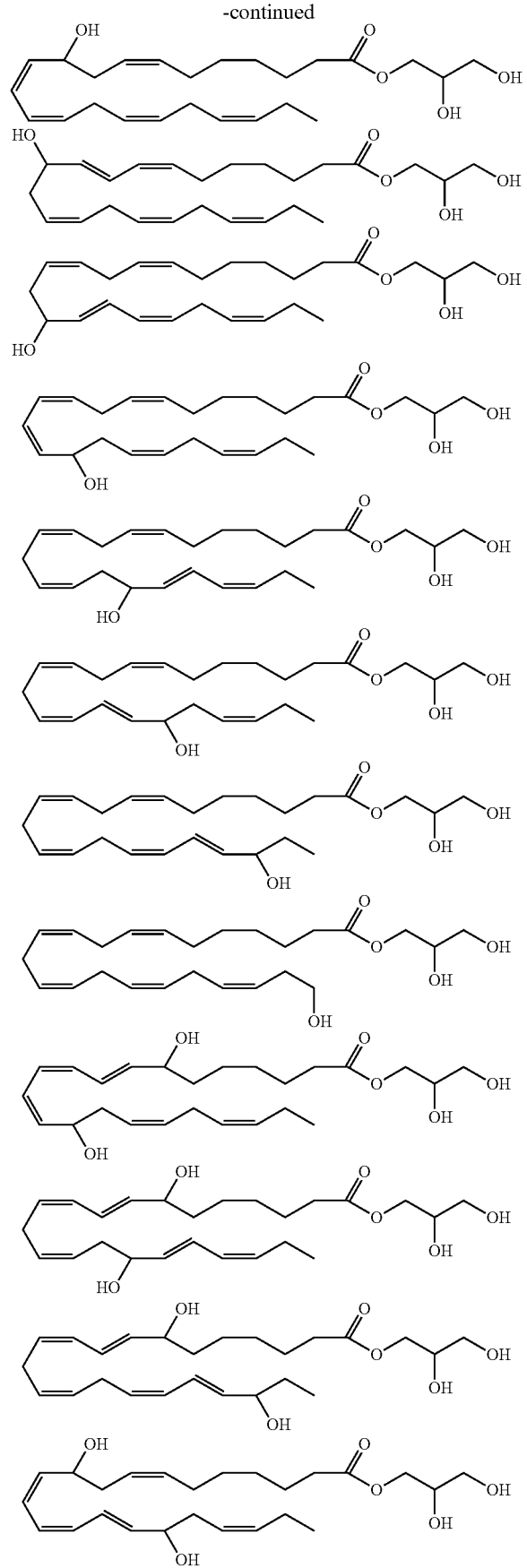
-continued
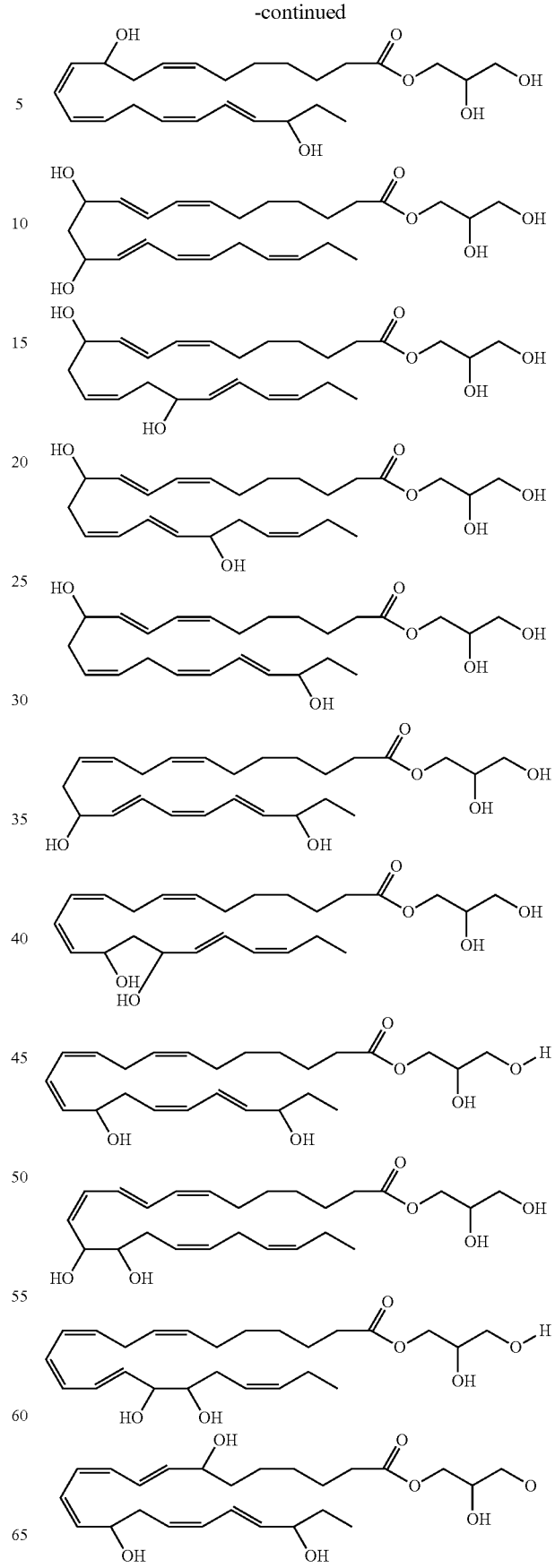

-continued
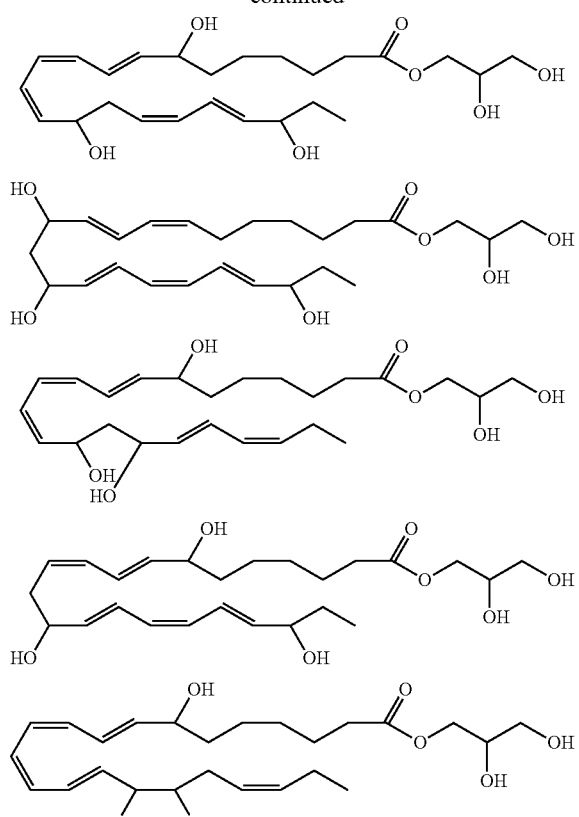
or a pharmaceutically acceptable salt thereof.
2. The compound of claim 1, wherein said compound is of formula:
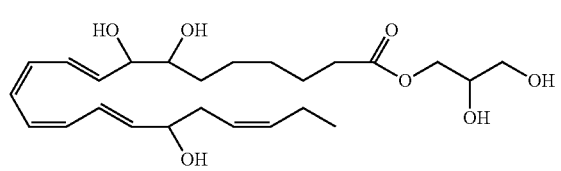
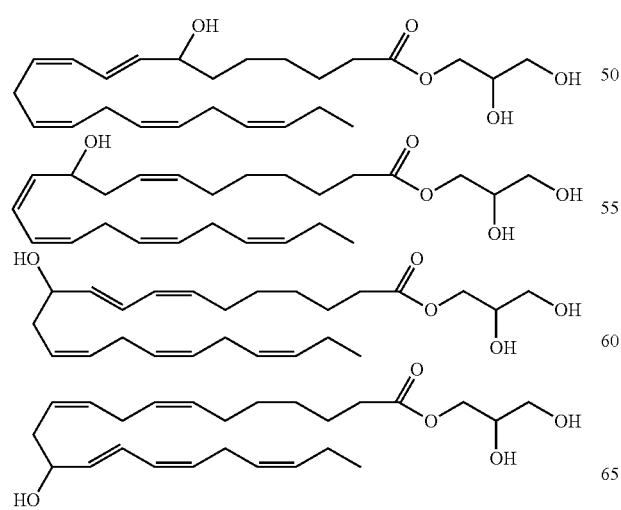
-continued
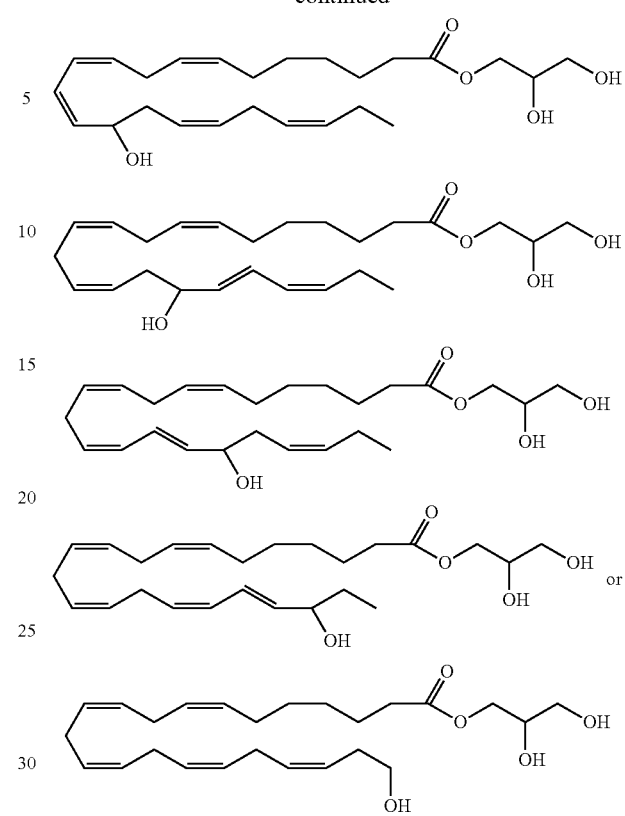
or a pharmaceutically acceptable salt thereof.
3. A compound of formula:
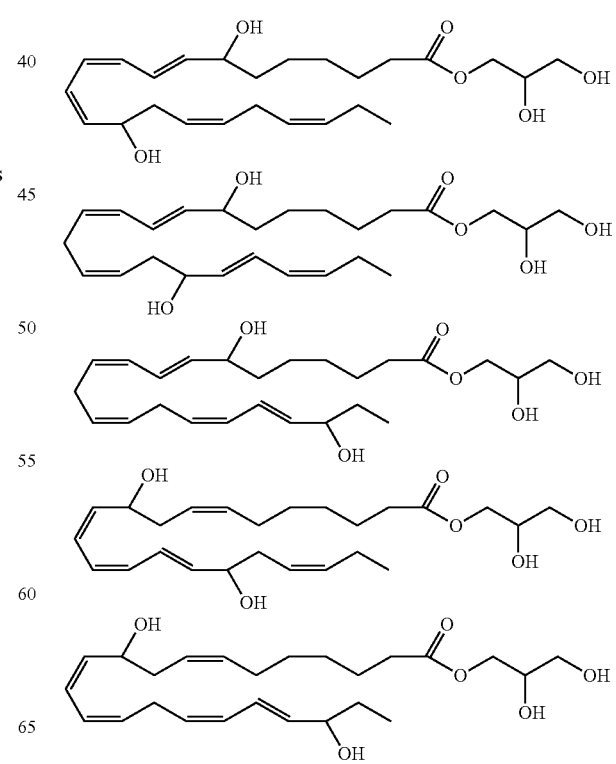

-continued

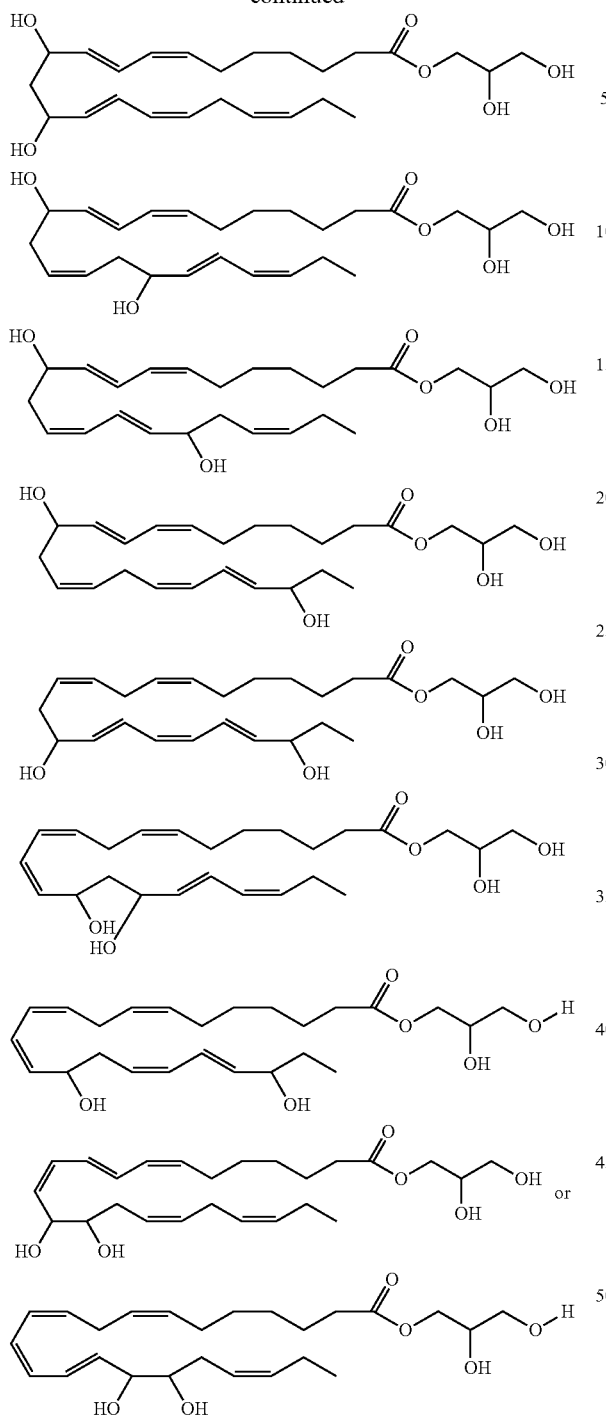

or a pharmaceutically acceptable salt thereof.

4. A compound of formula:

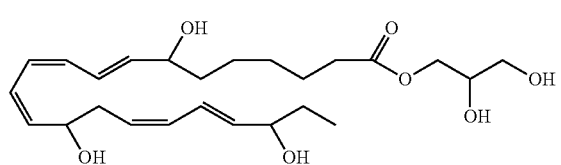

-continued

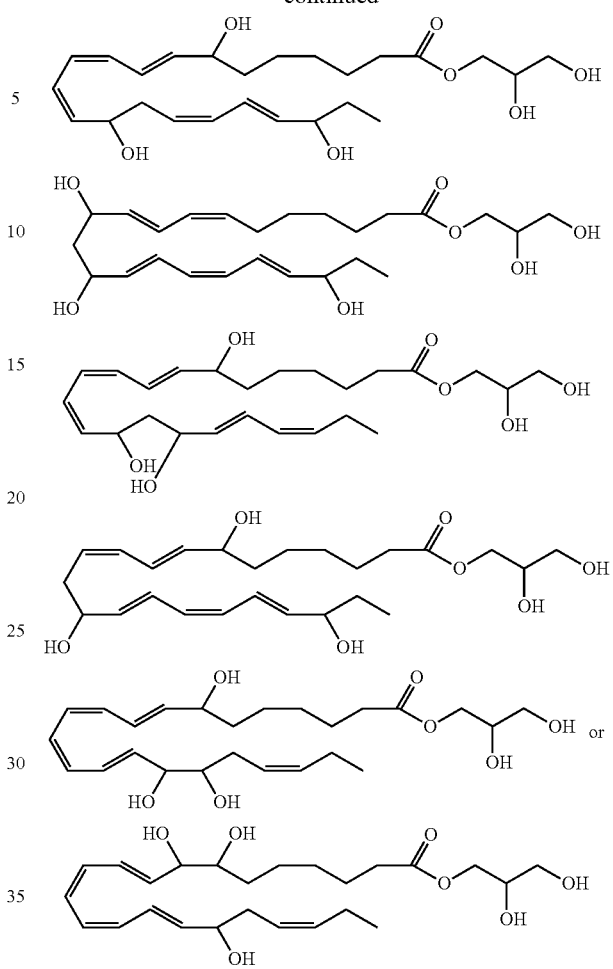

or a pharmaceutically acceptable salt thereof.

5. The compound of claim 1, wherein said compound is of formula:

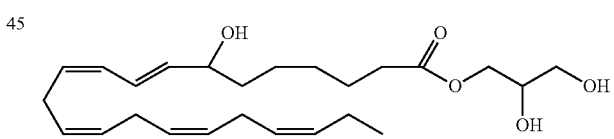

or a pharmaceutically acceptable salt thereof.

6. The compound of claim 1, wherein said compound is of formula:

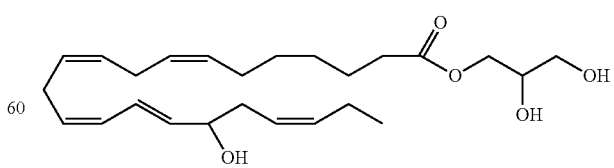

or a pharmaceutically acceptable salt thereof.

7. The compound of claim 1, wherein said compound is of formula:

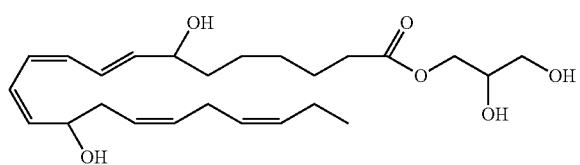 [SMILES: CC/C=C\C/C=C\CC(O)\C=C/C=C\C=C\C(O)CCCCCC(=O)OCC(O)CO]

or a pharmaceutically acceptable salt thereof.

8. The compound of claim 1, wherein said compound is of formula:

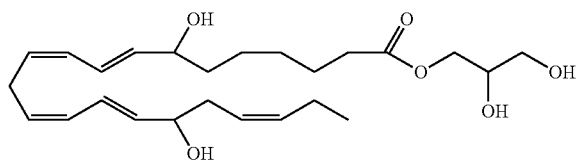 [SMILES: CC/C=C\CC(O)/C=C/C=C\C/C=C\C=C\C(O)CCCCCC(=O)OCC(O)CO]

or a pharmaceutically acceptable salt thereof.

9. The compound of claim 1, wherein said compound is of formula:

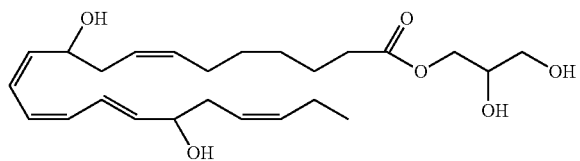 [SMILES: CC/C=C\CC(O)/C=C/C=C\C=C/C(O)C/C=C\CCCCCC(=O)OCC(O)CO]

or a pharmaceutically acceptable salt thereof.

10. The compound of claim 1, wherein said compound is of formula:

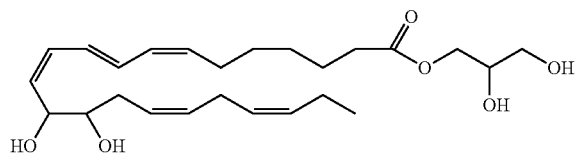 [SMILES: CC/C=C\C/C=C\CC(O)C(O)\C=C/C=C/C=C\CCCCCC(=O)OCC(O)CO]

or a pharmaceutically acceptable salt thereof.

11. The compound of claim 1, wherein said compound is of formula:

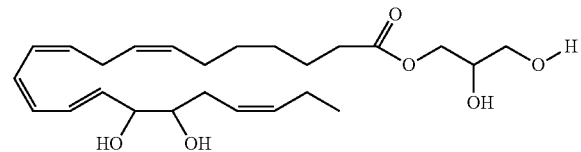 [SMILES: CC/C=C\CC(O)C(O)/C=C/C=C\C=C/C/C=C\CCCCCC(=O)OCC(O)CO]

or a pharmaceutically acceptable salt thereof.

12. The compound of claim 1, wherein said compound is of formula:

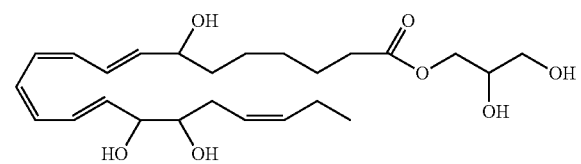 [SMILES: CC/C=C\CC(O)C(O)/C=C/C=C\C=C/C=C/C(O)CCCCCC(=O)OCC(O)CO]

or a pharmaceutically acceptable salt thereof.

13. The compound of claim 1, wherein said compound is of formula:

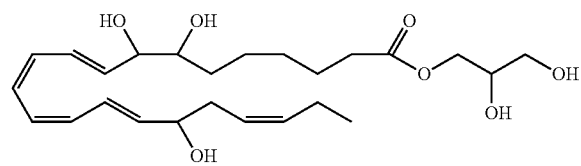 [SMILES: CC/C=C\CC(O)/C=C/C=C\C=C/C=C/C(O)C(O)CCCCCC(=O)OCC(O)CO]

or a pharmaceutically acceptable salt thereof.

* * * * *